United States Patent [19]

Onishi et al.

[11] Patent Number: 4,789,239

[45] Date of Patent: Dec. 6, 1988

[54] EMISSION SPECTROSCOPIC ANALYZER

[75] Inventors: Koichi Onishi, Katsuta; Yoshifusa Ouchi, Ibaraki; Takashi Suganuma, Katsuta; Atsushi Utsumi, Kawanishi; Takao Kuroiwa, Amagasaki, all of Japan

[73] Assignees: Mitsubishi Cable Industries, Ltd., Hyogo; Doryokuro Kakunenryo Kaihatsu Jigyodan, Tokyo, both of Japan

[21] Appl. No.: 901,679

[22] Filed: Aug. 29, 1986

Related U.S. Application Data

[63] Continuation-in-part of Ser. No. 503,017, Jun. 10, 1983, abandoned.

[51] Int. Cl.$^4$ .................. G01N 21/73; G01J 3/443
[52] U.S. Cl. .................... 356/316; 356/313
[58] Field of Search ............ 356/311, 313, 315, 316, 356/319, 326, 328, 417; 250/515.1

[56] References Cited

U.S. PATENT DOCUMENTS

| | | | |
|---|---|---|---|
| 2,484,003 | 10/1949 | Simison | 350/96.24 |
| 3,004,368 | 10/1961 | Hicks, Jr. | 250/96.24 |
| 3,216,807 | 11/1965 | Woodcock | 350/96.24 |
| 3,279,460 | 10/1966 | Sheldon | 128/6 |
| 3,504,060 | 3/1970 | Gardner | 350/96.24 |
| 3,692,415 | 9/1972 | Shiller | 356/417 |
| 3,723,007 | 3/1973 | Leonard | 356/301 |
| 3,758,188 | 9/1973 | Koester | 350/96.25 |
| 3,819,442 | 6/1974 | Brushenko | 350/96.24 |
| 3,909,133 | 9/1975 | Hobson et al. | 356/313 |
| 3,942,892 | 3/1976 | Ambrose et al. | 356/313 |
| 4,076,377 | 2/1978 | Moraschetti | 350/96.25 |
| 4,113,350 | 9/1978 | Haines | 350/96.29 |
| 4,256,404 | 3/1981 | Walker | 356/316 |
| 4,326,802 | 4/1982 | Smith, Jr. et al. | 356/316 |
| 4,375,919 | 3/1983 | Busch | 356/328 |
| 4,378,952 | 4/1983 | Siegmund | 350/96.25 |
| 4,395,005 | 7/1983 | Ganssle | 350/96.25 |
| 4,432,644 | 2/1984 | Demers et al. | 356/316 |
| 4,452,623 | 6/1984 | Utsumi et al. | 65/4.21 |
| 4,470,699 | 9/1984 | Gay | 356/316 |
| 4,623,250 | 11/1986 | Onishi et al. | 356/316 |

FOREIGN PATENT DOCUMENTS

| | | | |
|---|---|---|---|
| 0072405 | 6/1981 | Japan | 350/96.24 |
| 0207849 | 12/1982 | Japan | 356/316 |
| 0094042 | 5/1984 | Japan | 356/316 |
| 7603893 | 10/1976 | Netherlands | 356/417 |
| 2104676 | 3/1983 | United Kingdom | 350/96.29 |
| 8200898 | 3/1982 | World Int. Prop. O. | |

OTHER PUBLICATIONS

Adrain et al., Laser & Elektro-Optik, vol. 12, No. 3, pp. 5–9, Sep. 1980.
"Improvement in the Analyses of Metal", Anon, Industrial Opportunities Ltd. Research Disclosure, No. 124, p. 12, Aug. 1974.

Primary Examiner—F. L. Evans
Attorney, Agent, or Firm—Armstrong, Nikaido, Marmelstein & Kubovcik

[57] ABSTRACT

Radioactive materials can be safely analyzed by an emission spectroscopic analyzer comprising an exciting device for exciting a radioactive material to be analyzed to emit light. The exciting device is enclosed in a radiation shielding wall. A detecting device detects the emitted light. The detecting device is located outside the radiation shielding wall. A light-transmitting device is provided between the exciting device and the detecting device such that the emitted light impinging on a first end of the light-transmitting device will be received at the detecting device as light having been transmitted through the light-transmitting device and emitted from a second end of the light-transmitting device. The light-transmitting device penetrates a hole made in the radiation shielding wall which has a sealing structure to prevent radiation leakage. The light-transmitting device penetrates the hole with a curvature. A lens system is attached to the second end of the light-transmitting device to permit visual observation of the emitted light therethrough. A fine adjustment device adjusts the position of the first end of the light-transmitting device in relation to the emitted light from the material to be analyzed.

11 Claims, 5 Drawing Sheets

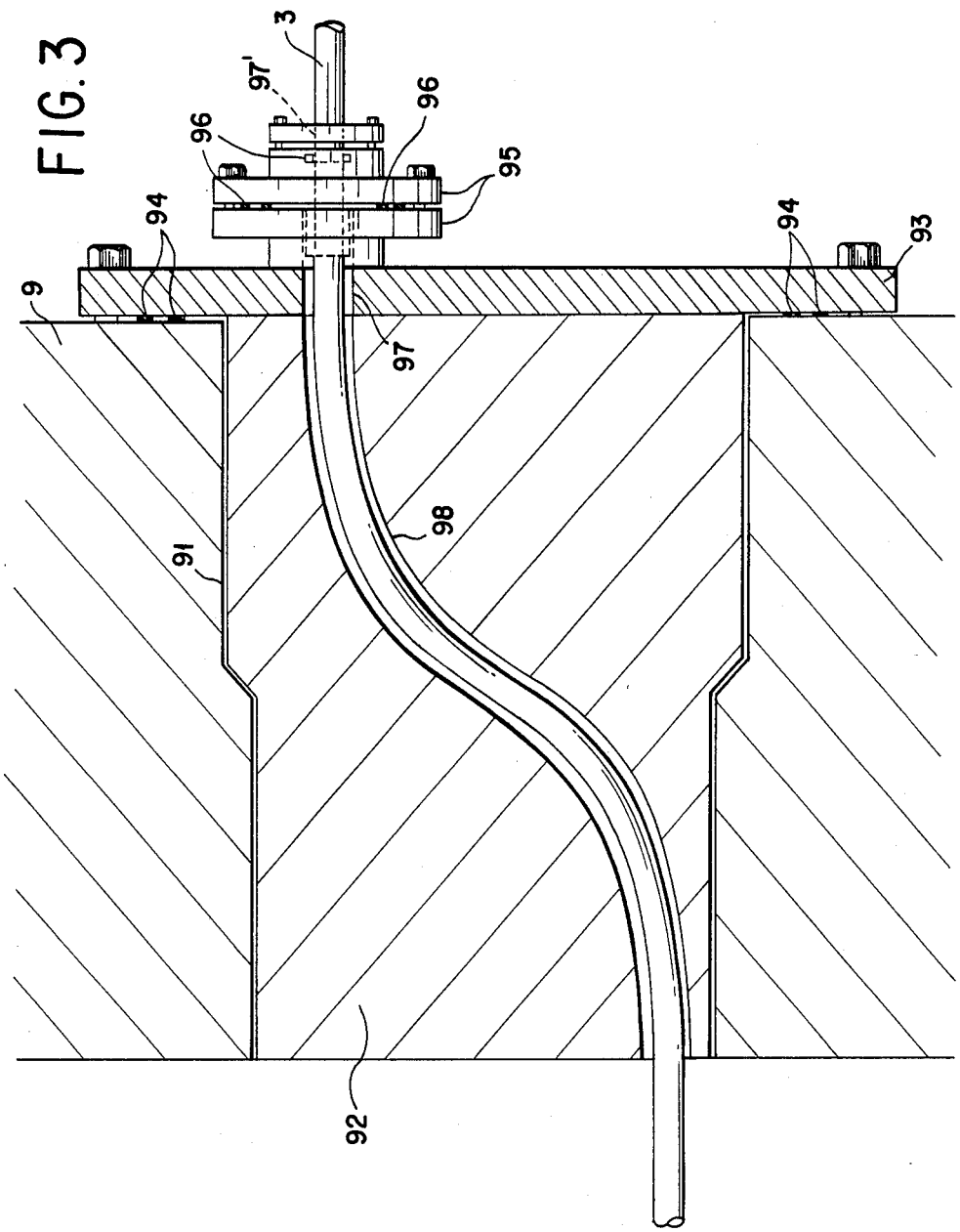

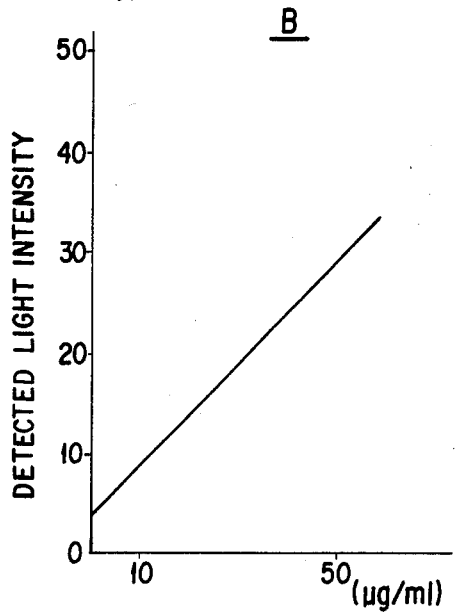
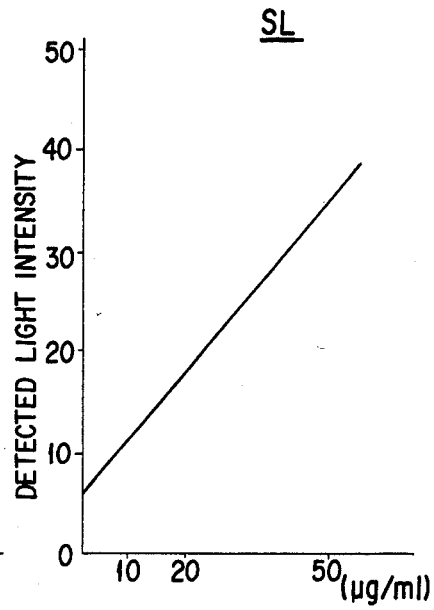
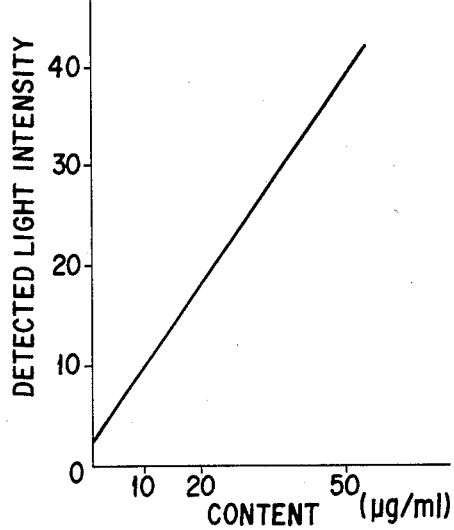
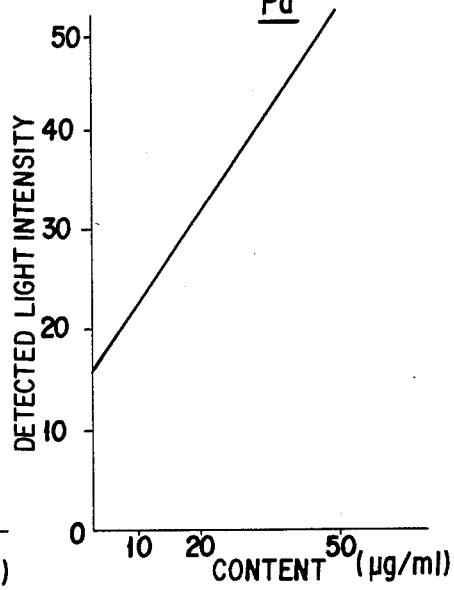

EMISSION SPECTROSCOPIC ANALYZER

BACKGROUND OF THE INVENTION

1. Field of the Invention

This application is a continuation-in-part application, Ser. No. 503,017, filed June 10, 1983, now abandoned, and relates to an emission spectroscopic analyzer. More particularly, it relates to an emission spectroscopic analyzer comprising a device for exciting a radioactive material to be analyzed to emit light, a device for detecting the emitted light wherein the emitted light is transmitted from the exciting to the detecting means through light-transmitting the device, and means for exciting the radioactive material is surrounded by a radiation shielding wall through which light-transmitting means penetrates.

2. Description of the Prior Arts

Analysis of high-level radioactive materials in an atomic energy related field is accompanied by remote-controlled analysis with use of a hot cell in order to avoid and prevent irradiation. Conventional titrimetric or calorimetric analysis is a manual operated analysis designed to be employed in a laboratory but hardly applied to the analysis of the radioactive materials. Further, these analytical methods have some disadvantages such that their procedures are complicated, and only a small number of materials can be analyzed.

On the other hand, emission spectroscopic analysis, in which a material to be analyzed is excited to emit light and the wave length and intensity of the spectrum of the emitted light are measured so as to determine the kinds and contents of the component elements in the material, can be employed for a wide range of concentration of the material and simultaneously analyze plural elements. Further, it is not affected by the high-level radiation. It is, however, difficult to set up the whole emission spectroscopic analyzer in the hot cell, since the high temperature and humidity and/or the presence of acidic vapor deteriorate the accuracy of the analysis and make the maintenance of the analyzer extremely difficult. It may be possible to separate the exciting means from the detecting means and to locate the former in the hot cell and the latter outside it. However, this is also difficult due to attentuation of the transmitted light through a longer transmitting path and difficulty of radiation shielding.

SUMMARY OF THE INVENTION

One object of the present invention is to provide an emission spectrosopic analyzer which can remotely analyze radioactive materials in a hot cell in a high radiation atmosphere.

Another object of the present invention is to provide an emission spectroscopic analyzer which is not affected by atmospheric conditions surrounding the radioactive materials to be analyzed.

These and other objects are accomplished by an emission spectroscopic analyzer comprising:

a device for exciting a radioactive material to be analyzed to emit light, which is enclosed in a radiation shielding wall;

a device for detecting the emitted light, which is located outside the radiation shielding wall;

a light-transmitting device provided between the exciting device and the detecting device such that the emitted light impinging on a first end of the light-transmitting device disposed at the exciting device will be received at the detecting device as light having been transmitted through the light-transmitting device and emitted from a second end of the light-transmitting device disposed at the detecting device and penetrating a hole made in the radiation shielding wall having a sealing structure to prevent radiation leakage, the light-transmitting device penetrating the hole with curvature;

a lens system attached to the second end of the light-transmitting device to permit visual observation of the emitted light therethrough; and a fine adjustment device for adjusting the position of the first end of the light-transmitting device in relation to the emitted light from the material to be analyzed.

The light-transmitting device is an image guide formed of a bundle of a plurality of optical fibers in which the position of each optical fiber in relation to other optical fiber at one end of the image guide exactly corresponds to that position of each optical fiber in relation to other optical fibers at another end of the image guide. The bundle of optical fibers is comprised of plural silica glass fibers fused together to form a single unit. Each silica glass fiber has a core section of pure silica and a cladding section surrounding the core section and made of silica glass having a refractive index less than the refractive index of the core section. The second end of the light-transmitting means is detachably mounted to the detecting device so that the lens system may be attached to the detached second end of the light-transmitting device for viewing of images transmitted through the light-transmitting device. The optimum position of the first end of the light-transmitting device may be adjusted with the fine adjusting device to view a desired image through the lens system and upon viewing of the desired image the lens system may be detached and the second end of the light-transmitting device may be attached to the detecting device for detecting emitted light of the desired image.

BRIEF DESCRIPTION OF DRAWINGS

FIGS. 4A to 4H are calibration lines for boron, silicon, molybdenum, palladium, aluminum, cerium, lithium and potassium, respectively.

DETAILED DESCRIPTION OF THE INVENTION

Figure 1:
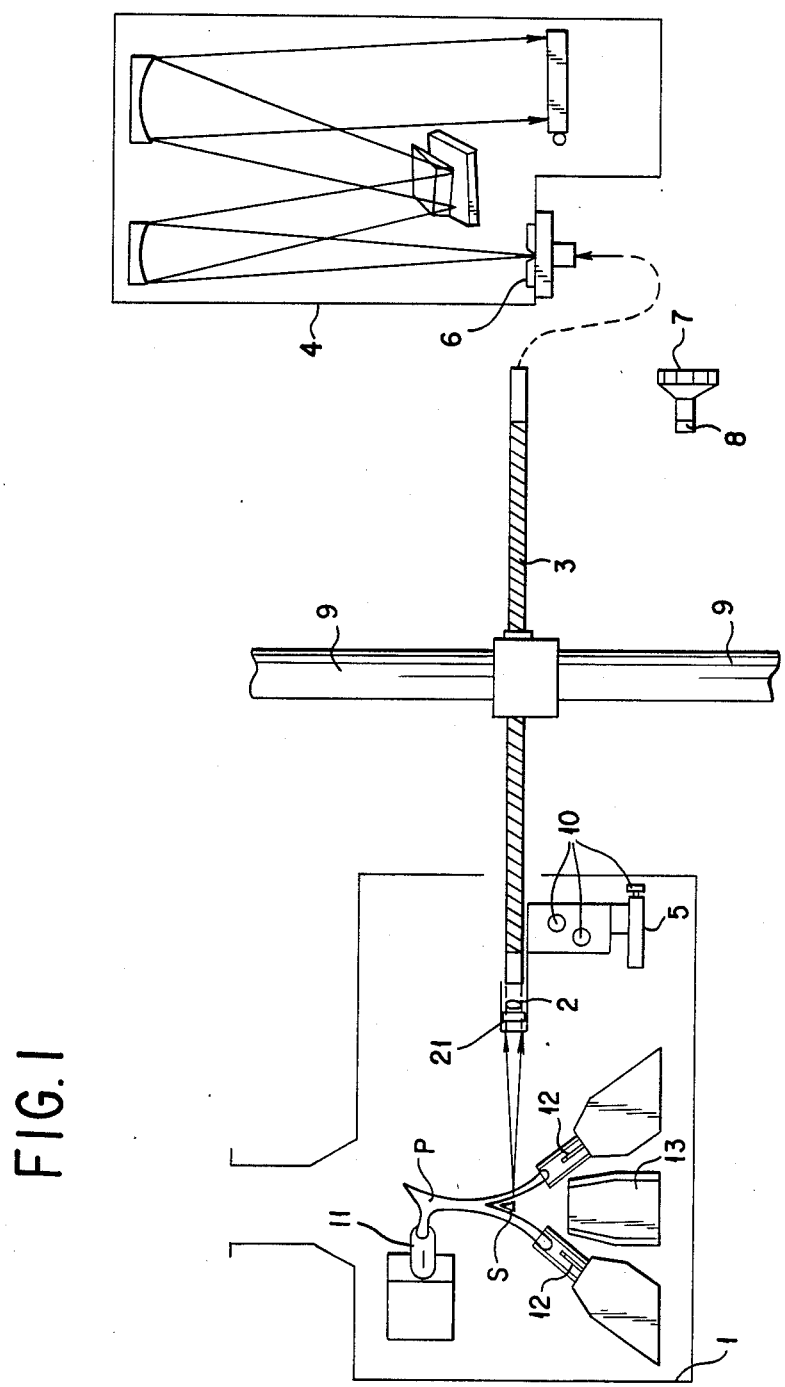
FIG. 1 schematically shows an emission spectroscopic analyzer of the present invention.

In the analyzer according to the present invention, the exciting means may be any one that is used in the conventional emission spectroscopic analyzer, and its examples are direct current arc (DCA), high voltage spark (HVS), direct current plasma (DCP), inductively coupled plasma (ICP), etc. When the radioactive material to be analyzed is in a liquid state such as a solution of the material, preferred exciting means is plasma of an inert gas such as argon. When the sample is in a solid state, preferred exciting means is electrical discharge such as arc discharge.

The light-transmitting means is an image guide formed of a bundle of a plurality of optical fibers in which the position of each optical fiber in relation to other optical fiber at one end of the image guide exactly corresponds to the position of each optical fiber in relation to other optical fibers at another end of the image guide so that it can transmit light as an image.

Since a light guide or a rod fiber transmits the intensity of light but not as an image, it cannot pick up a normal position of the emitted light or the emitted light from the material selectively. Namely the light emitted from the material and that emitted from the exciting means such as plasma simultaneously impinge on the end of the optical fiber(s), so that an S/N ratio is deteriorated. On the contrary, the image guide can catch the image of light in the normal position and transmit it. When a narrow image angle lens system is provided with at the end of the image guide near the exciting means, the position of the end of the guide can be adjusted so as to selectively pick up the light emitted from the material to be analyzed and not to pick up the light emitted from th exciting means, which allows the precise analysis with a low S/N ratio.

The bundle of optical fibers is comprised of plural silica glass fibers, for example, about 1,000 to 150,000 optical fibers fused together to form a single unit. Each silica glass fiber has a core section of pure silica for transmitting light and a cladding section surrounding the core section and made of silica glass having a refractive index less than the refractive index of the core section. An outer diameter of each optical fiber is usually from 5 to 50 microns. The optical fiber may further comprises a protective layer surrounding the cladding section. The silica glass fiber is used according to the present invention since it has better radiation and heat resistance, lower transmission loss and better absorption properties of ultraviolet light and shows stabilized transmission properties. The image guide includes a flexible one in which the optical fibers are stuck together only at the both ends and a slightly rigid one in which the optical fibers are fused together along its whole length. Generally, the latter is preferred, since it has superior heat resistance, mechanical strength and resistance of breakage of each fiber in use so that it can transmit clearer image than the former.

The detecting means may be any of conventional detecting means which can detect the emitted spectral lines. From the detected spectral lines, the kinds and the contents of the component elements in the radioactive material can be determined.

The present invention will be described, by way of example, with reference to the accompanying drawings.

In an emission spectroscopic analyzer of FIG. 1, a direct current plasma-generating device 1 comprises a tungsten-made cathode 11, graphite-made anodes 12, 12 and a nozzle 13 for gushing an atomized sample. As an ionizable gas, argon gas (Ar) is gushed through nozzles along the electrodes 12, 12. As soon as the direct current arc is generated between the cathodes 11 and the anodes 12, 12, the argon gas is ionized to form plasma (P). Then, the radioactive sample to be analyzed is atomized by means of a ceramic nebulizer (not shown), introduced into the argon plasma and excited to emit light. According to the present invention, the means for exciting the radioactive material is shielded by a wall 9 made of heavy concrete having a thickness of at least about 1 meter to prevent the radiation leakage. The excitation light (S) generated by the means for exciting the material in the shielding wall is transmitted to a spectrometer 4 through the light-transmitting means 3 as hereinafter described.

Figure 2:
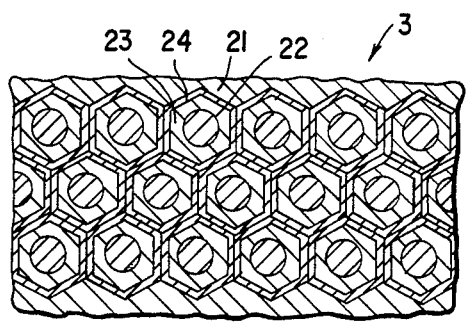
FIG. 2 is a partial cross section of an image guide used as light-transmitting means of the analyzer of the present invention, FIG. 3 schematically shows a through structure made in the shielding wall through which light-transmitting means penetrates.
Figure 4E:
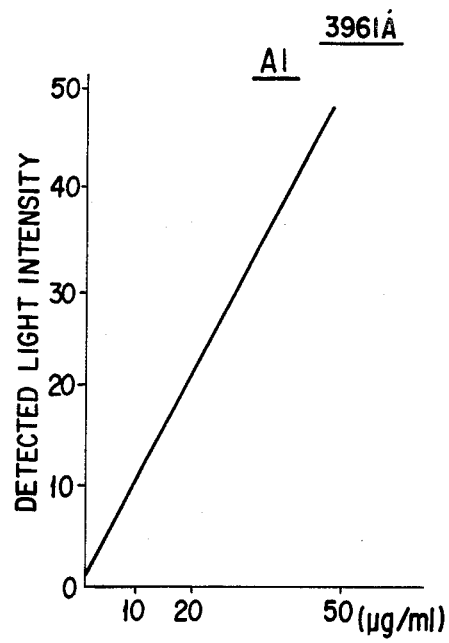
Figure 4F:
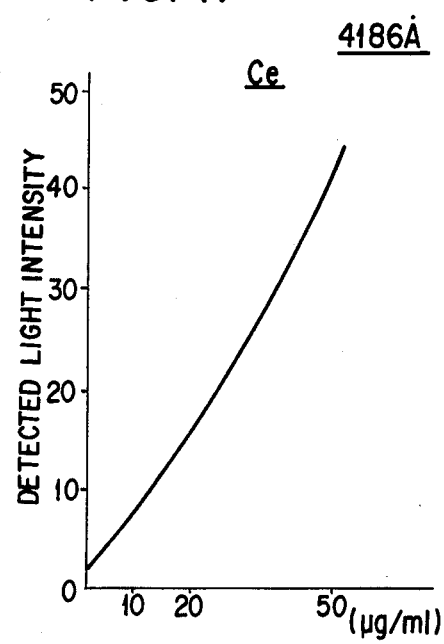
Figure 4G:
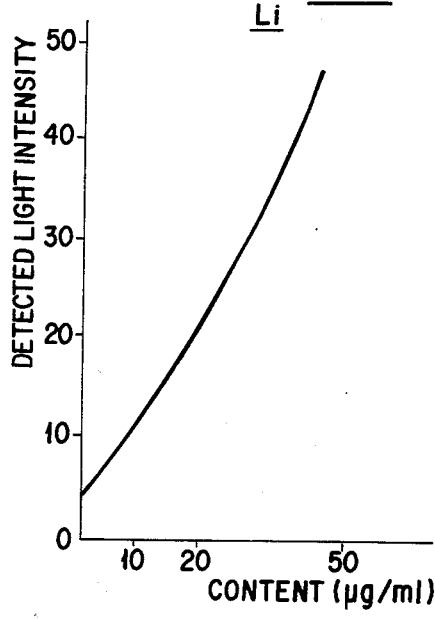
Figure 4H:
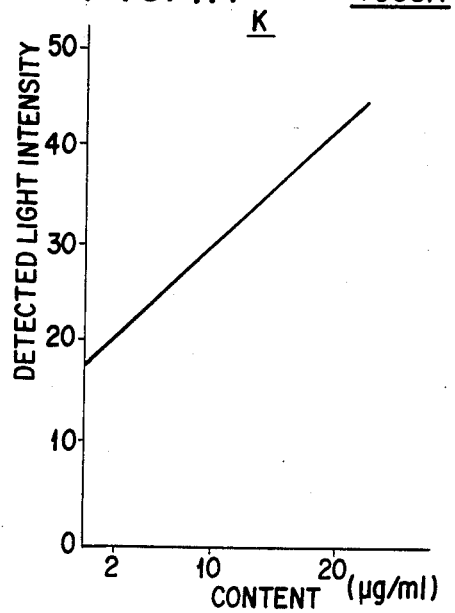

The light-transmitting means 3 is an image guide consisting of a bundle of silica glass optical fibers, a partial cross section of which is shown in FIG. 2. An optical fiber 21 comprises a core 22 comprising pure silica glass, a cladding 23 surrounding the core 22 and a supporting layer 24 surrounding the cladding 23. The cladding comprises silica glass doped with a conventional dopant to lower the refractive index of the pure silica glass. Thus, the refractive index of the cladding may be adjusted by selecting a kind and an amount of the dopant. The supporting means 24 comprises pure silica glass and prevents damages and/or disorder of the arrangement of the optical fibers when they are fused together. The image guide shown in FIG. 2 may be produced by inserting a number of optical fiber preforms each comprising the core, the cladding and the supporting layer in a silica glass-made tube, heating the tube including the optical fibers and drawing it to reduce the diameter and to fuse the adjacent fibers together.

The excitation light (S) from the radioactive material impinges at the first end of the image guide near the exciting means and propagates through the image guide to the spectrometer 4 with transmitting the light in the form of an image to the second end of the image guide from which the light exits. At this stage, the second end of the image guide is detached from the spectrometer 4 (for example, GEW-170 manufactured by Shimadzu Corporation) and attached to a lens system 7 which may include a color filter 8 for visual inspection. Thereby, the optimum position of the first end of the image guide is visually determined through the filter by adjusting the position of the first end by means of the fine adjustment device 5. After the optimum position of the first end of the image guide is determined, the second end of the image guide is detached from the lens system 7 and reattached to the spectrometer 4.

The first end of the image guide is placed in a plasma generating apparatus 1 and at the tip of the first end, the condenser lens 2 is attached to collect the excitation light from the excited material. The condenser lens 2 should be resistant to radiation in the plasma generating apparatus 1 and preferably made of synthetic quartz glass. In front of the condenser lens 2, detachably attached may be a plate made of synthetic quartz glass 21 for protecting the lens from radiation heat generated by the plasma in the plasma generating apparatus and suspended dust liberated rated from the sample to be analyzed and supplied in the plasma. A position of first end of the image guide in the plasma generating apparatus is adjusted by means of a fine adjustment device 5 so that it is optimized to receive the excitation light (S). The fine adjustment device can triaxially move the first end of the image guide by means of moving handles 10.

The positioning of the first end of the image guide with the moving handles can be remotely operated by means of manipulators (not shown) from outside of the heavy concrete wall of the plasma generating apparatus with viewing the image of the excitation light (S) at the second end of the image guide since the inside of the heavy concrete wall is occupied by a radiation atmosphere.

A part of the heavy concrete wall through which the image guide passes has a through structure as shown in FIG. 3 so as to shield the strong radiation and keep air tightness of the plasma generating apparatus in view of accuracy of analysis.

In FIG. 3, a separating wall 9 has a through hole 91, through which a cylindrical through plug 92 is inserted. The plug 92 is made of a material with radiation resistance and a shielding effect such as stainless steel and lead. Preferably, the plug has a stepped shape as shown in FIG. 3 rather than a straight cylindrical shape so as to prevent leakage of radiation from the plasma generating apparatus. This is because the radiation directly advances. At the side of the spectrometer, there is provided a flange 93 having a diameter larger than the outer diameter of the plug. The flange can be integrally made with the plug. The flange and the heavy concrete wall 9 are bolted with sealing them by an O-ring 94 made of a resilient radiation resistant material such as neoprene.

Near the periphery of the flange 93, attached is a plug 95 for inserting the image guide, each elements of which are shield by O-rings 96 as shown in FIG. 3.

The image guide inserting plug 95 and the flange 93 of the through plug have holes 97,97'. On the peripheral surface of the through plug 92, a groove 98 is made in which the image guide is passed. Preferably, the groove 98 is of a non-straight shape to prevent direct advance of radiation. If the groove is of a straight shape and the sealing of the through plug or the image guide inserting plug is not sufficient, radiation directly advances outside. The non-straight shape may be a helical shape as shown in FIG. 3, a S-shape or a U-shape. Instead of the peripheral groove, a through hole may be bored through the plug 92.

The image transmitted through the image guide 3 is emitted from the second end thereof and received by the spectrometer 4. The kinds and the amounts of the component elements in the sample can be determined from the measured spectral lines and their intensity according to a conventional manner.

FIGS. 4A to 4H show examples of calibration lines for boron (2,496 A), silicon (2,881 A), molybdenum (3,132 A), palladium (3,403 A), aluminum (3,961 A), cerium (4,186 A), lithium (6,103 A) and potassium (7,698 A) determined by the analyzer shown in FIG. 1.

When the relation between the intensity of the detected light described as above and the content of various atoms is stored by a computer, kinds and contents of atoms contained in the sample can be easily calculated from the wavelength and the intensity of the spectrum lines observed by the analyzer according to the present invention.

According to the present invention, the emission spectroscopic analysis can be carried out precisely and safely under harsh condition in the hot cell.

What is claimed is:

1. An emission spectroscopic analyzer comprising:
    exciting means for exciting a radioactive material to be analyzed to emit light, said exciting means being enclosed in a radiation shielding wall;
    detecting means for detecting the emitted light, said detecting means being located outside the radiation shielding wall;
    light-transmitting means having a first end disposed at the exciting means and having a second end disposed at the detecting means, said light-transmitting means for transmitting the emitted light, impinging on the first end of the light-transmitting means, to the detecting means as light having been transmitted through the light-transmitting means and emitted from the second end of the light-transmitting means, said light-transmitting means penetrating a hole made in the radiation shielding wall having a sealing structure to prevent radiation leakage, the light-transmitting means penetrating the hole with curvature;
    a lens system for detachable connection to the second end of the light-transmitting means to permit visual observation of the emitted light therethrough; and
    a fine adjustment device for adjusting the position of the first end of the light-transmitting means in relation to the emitted light from the material to be analyzed;
    wherein the light-transmitting means is an image guide formed of a bundle of a plurality of optical fibers in which the position of each optical fiber in relation to other optical fiber at one end of the image guide exactly corresponds to that position of each optical fiber in relation to other optical fibers at another end of the image guide, the bundle of optical fibers being comprised of plural silica glass fibers fused together to form a single unit, each silica glass fiber having a core section of pure silica and a cladding section surrounding the core section and made of silica glass having a refractive index less than the refractive index of the core section, and wherein the second end of the light-transmitting means is arranged to be detachably mounted to the detecting means so that the lens system may be attached to the second end of the light-transmitting means when the second end is detached from the detecting means for viewing of images transmitted through the light-transmitting means, whereby the optimum position of the first end of the light-transmitting means may be adjusted with the fine adjusting device to view a desired image through the lens system and upon viewing of the desired image, the lens system may be detached from the second end and the second end of the light-transmitting means may be attached to the detecting means for detecting emitted light of the desired image.

2. The emission spectroscopic analyzer according to claim 1, wherein a condenser lens is attached to the tip of the first end of the light-transmitting means near the exciting means.

3. The emission spectroscopic analyzer according to claim 2, wherein the condenser lens is made of synthetic quartz glass.

4. The emission spectroscopic analyzer according to claim 2, wherein a plate of synthetic quartz glass is placed in front of the condenser lens.

5. The emission spectroscopic analyzer according to claim 1, wherein the sealing structure of the hole through which the light-transmitting means penetrates comprises a plug inserted in the hole, and the plug has a helical groove on its peripheral surface so that the light transmitting means is placed in the groove.

6. The emission spectroscopic analyzer according to claim 1, wherein the position of the first end of the light-transmitting means in relation to the emitted light from the material to be analyzed is adjusted with the fine adjustment device which is remotely controlled.

7. The emission spectroscopic analyzer according to claim 1, wherein the exciting means is direct current plasma (DCP).

8. The emission spectroscopic analyzer according to claim 1, wherein the bundle of optical fibers is comprised of plural silica glass fibers fused together to form a single unit only at both ends of the bundle.

9. The emission spectroscopic analyzer according to claim 1, wherein the bundle of optical fibers is comprised of plural silica glass fibers fused together along the entire length of the bundle to form a slightly rigid unit.

10. The emission spectroscopic analyzer according to claim 1, wherein the lens system includes a color filter for visual inspection.

11. An emission spectroscopic analyzer comprising:

a radiation shielding wall having a hole therein and a sealing structure to prevent radiation leakage;

an exciting means for exciting a radioactive material to be analyzed to emit light, said exciting means being enclosed in said radiation shielding wall;

a detecting means for detecting the emitted light, said detecting means being located outside the radiation shielding wall;

a light-transmitting means having a first end disposed at the exciting means and having a second end disposed at the detecting means, said light-transmitting means for transmitting the emitted light from the exciting means to the detecting means, said emitted light impinging on the first end of the light-transmitting means and being transmitted through the light-transmitting means to be emitted from the second end of the light-transmitting means, said light-transmitting means penetrating said hole made in said radiation shielding wall, the light-transmitting means penetrating the hole with curvature;

a lens system for detachable connection to the second end of the light-transmitting means to permit visual observation of the emitted light therethrough; and a fine adjustment device for adjusting the position of the first end of the light-transmitting means in relation to the emitted light from the material to be analyzed, wherein the first end of the light-transmitting means is adjusted by the fine adjusting device to view a desired image through the lens system and upon viewing the desired image, the lens system is detached from the second end of the light-transmitting means and the second end is attached to the detecting means for detecing light of the desired image.

* * * * *